United States Patent

Palmieri et al.

[11] Patent Number: 5,004,469
[45] Date of Patent: Apr. 2, 1991

[54] IMPROVEMENTS IN AUTOMATIC MECHANICAL SUTURING GUNS

[75] Inventors: Beniamino Palmieri, Modena; Rodolfo Garlati, Olginate, both of Italy

[73] Assignee: Ricerche Biomediche S.r.l., Milan, Italy

[21] Appl. No.: 319,686

[22] Filed: Mar. 7, 1989

[51] Int. Cl.⁵ .............................................. A61B 17/00
[52] U.S. Cl. .................... 606/139; 606/142; 606/148
[58] Field of Search ............... 606/139, 142, 144, 148

[56] References Cited

U.S. PATENT DOCUMENTS

| | | | |
|---|---|---|---|
| 3,033,204 | 5/1962 | Wood | 606/139 |
| 3,687,138 | 8/1972 | Jarvik | 606/139 |
| 3,777,538 | 12/1973 | Weatherly et al. | 606/142 |
| 4,169,476 | 10/1979 | Hiltebrandt | 606/142 |
| 4,706,668 | 11/1987 | Backer | 606/142 |

Primary Examiner—Randall L. Green
Assistant Examiner—Gary Jackson
Attorney, Agent, or Firm—Wenderoth, Lind & Ponack

[57] ABSTRACT

A suturing gun which includes a conventional stitch applying device and comprises pliers for clamping the wound margins arranged close to the stitch outlet, further includes an external control element for actuating the pliers arranged at an easily accessible location for the surgeon when grasping the gun, and a driving system for transmitting the movement of the control element to the pliers. The suturing gun further comprises housing means for containing and retaining one or more gauze tampons, a first dispenser for containing and dispensing a disinfectant liquid or the like and a second dispenser for containing and dispensing a suture adhesive.

12 Claims, 4 Drawing Sheets

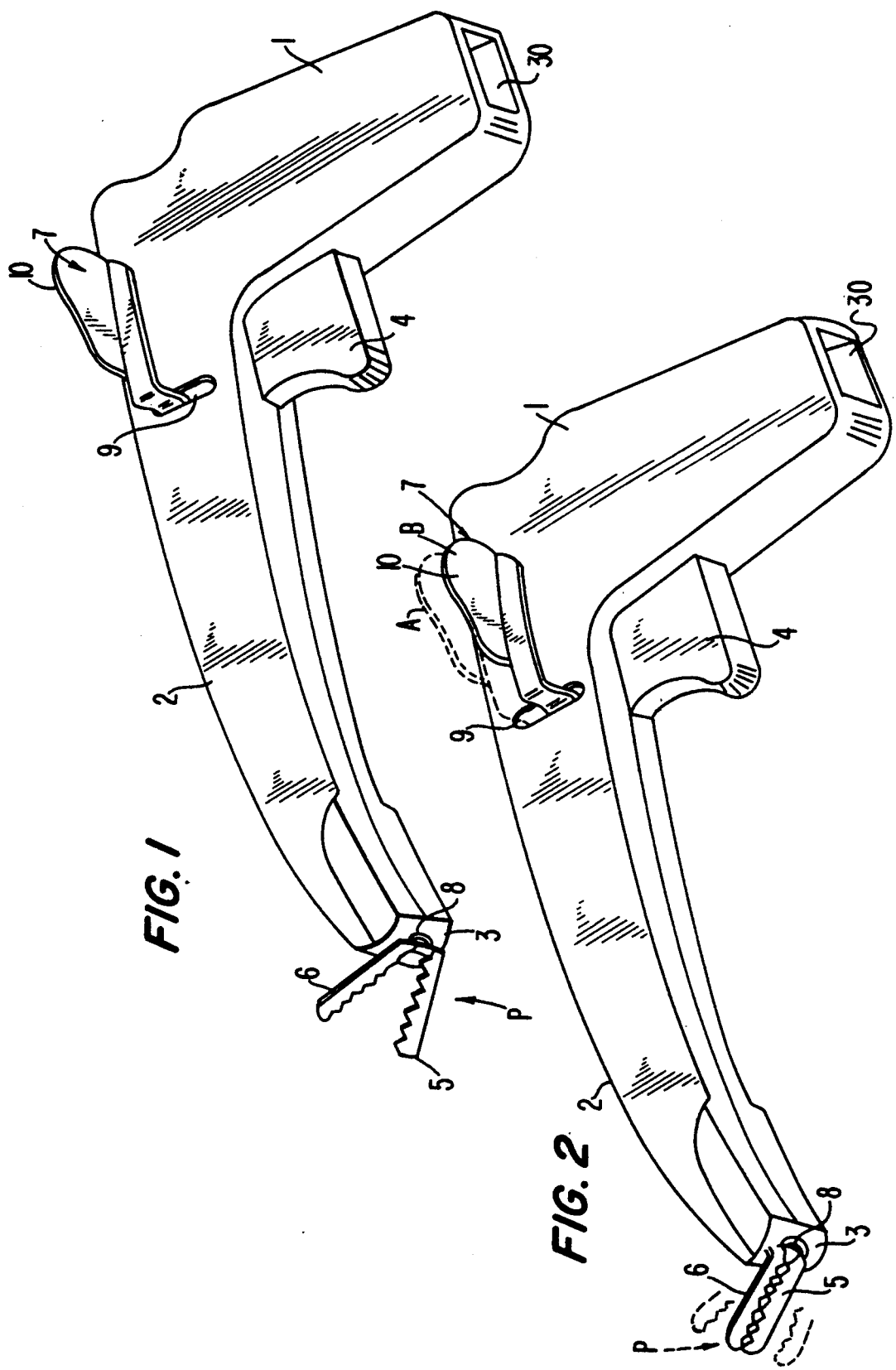

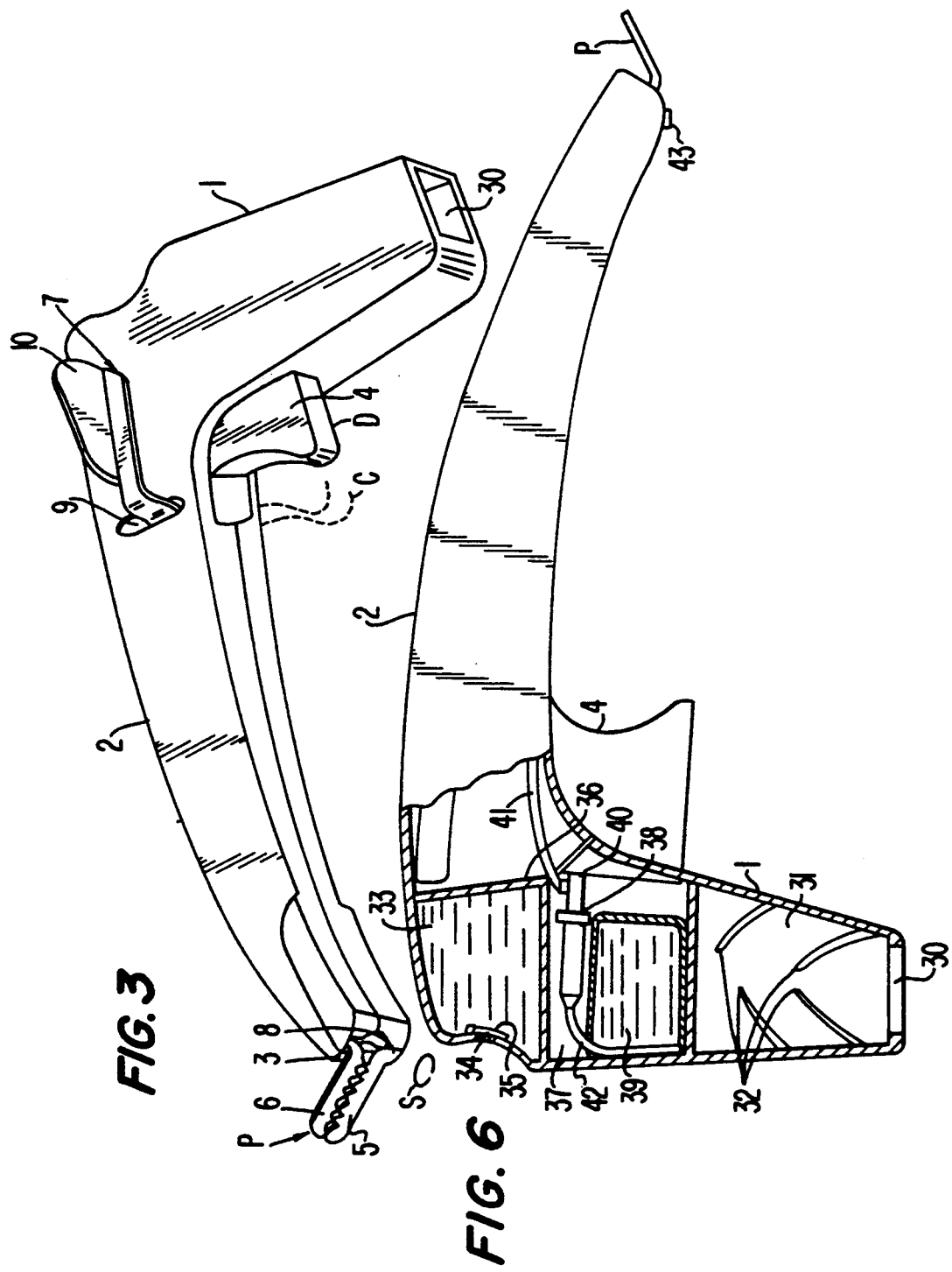

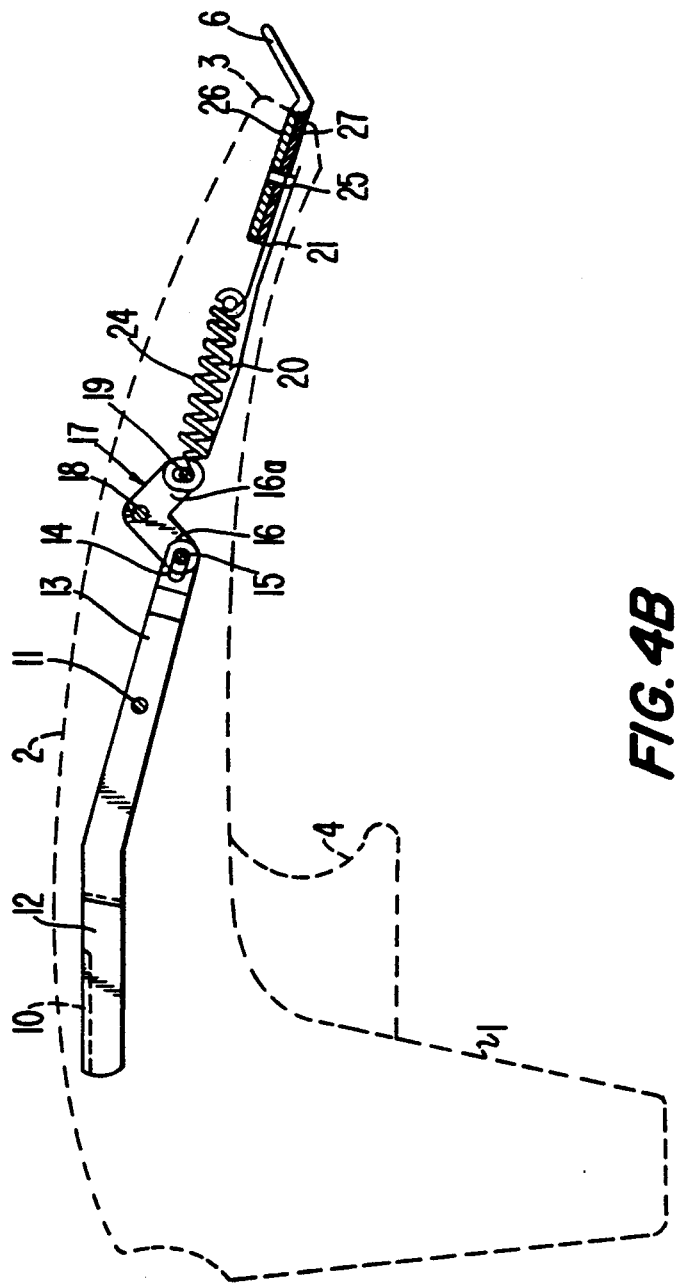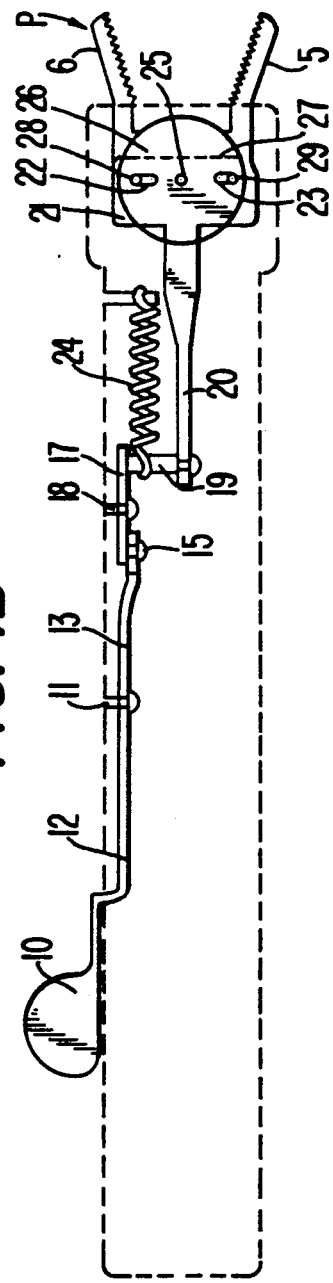

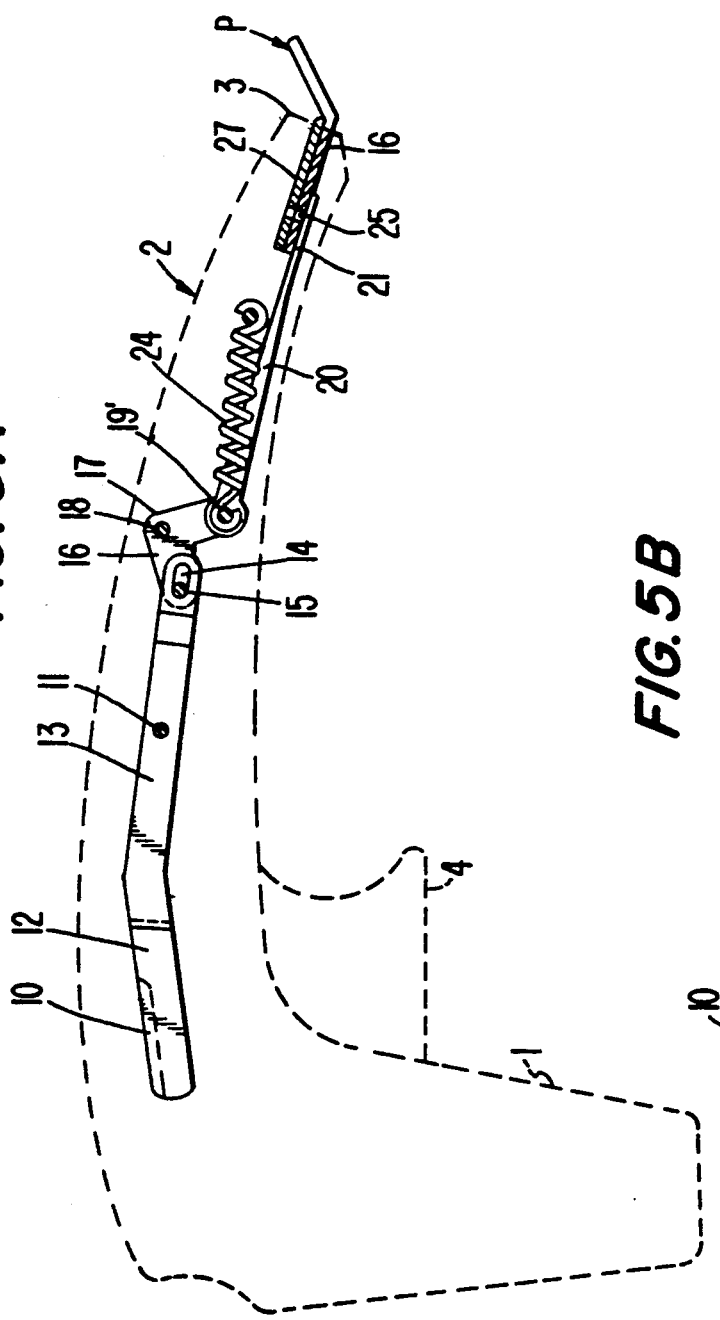
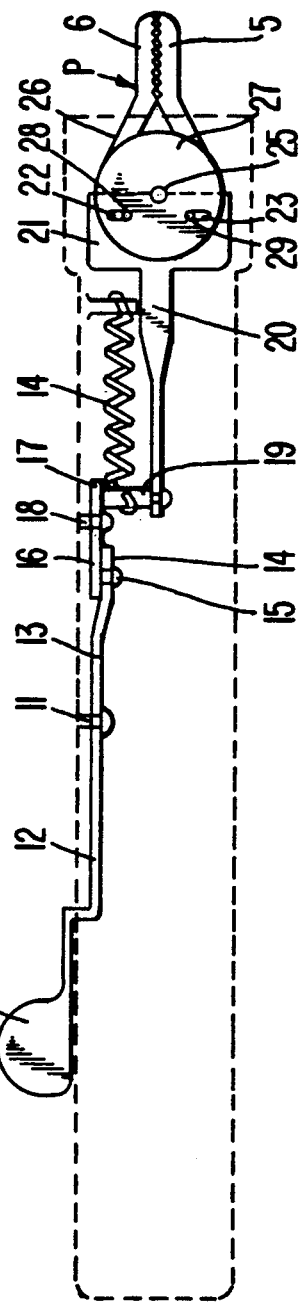

IMPROVEMENTS IN AUTOMATIC MECHANICAL SUTURING GUNS

BACKGROUND OF THE INVENTION

1. Field of the Invention

The present invention relates generally to suturing devices and, more particularly, to an improved suturing gun which can be operated with one hand so as to facilitate the suturing operation.

2. Description of the Prior Art

In the surgery field, mechanical suturing devices for suturing the skin are already known, and are generally produced in the shape of a gun. In use, a suturing gun of this kind is grasped by the surgeon with one hand, while he operates a forceps with the other hand in order to clamp the margins of the wounded skin together and maintain them in this clamped position so that the stitches delivered by the suturing gun can grip both the wound margins, such that the wound is properly closed. This procedure is very toilsome for the surgeon and often, to facilitate this operation, the mechanical suturing device is grasped by the right hand of the surgeon and the clamping of the skin margins is carried out by an assistant who operates a pair of toothed forceps to hold the wound margins clamped until the stitches have been applied. The latter solution facilitates the surgeon's task but requires the presence of two operators and therefore increases overall cost of the operation.

It is also known that during the suture operation the surgeon needs to have gauze tampons at his immediate disposal to plug the wound, as well as disinfectant liquids and suture adhesives in order to maintain the wound disinfected during the suture operation and sutured after the suture operation. The application of these products requires again the presence of a second operator during the suturing operation made by the surgeon, which operator must give the surgeon gauze tampons, disinfecting liquid and/or adhesive on request.

SUMMARY OF THE INVENTION

The present invention aims at obviating all the above mentioned disadvantages by providing a new and improved suturing gun which permits the suturing operation of a wound to be carried out by the surgeon with only one hand, thereby obtaining the advantages of better clamping the wound margins, facilitating the suturing operation and requiring less time for carrying out steps which can be performed simultaneously.

It is another object of the present invention to provide an improved suturing gun which permits the suturing operation of a wound to be carried out by the surgeon without the necessity of resorting to an assistant.

It is another object of the present invention to provide an improved suturing gun which permits the suturing operation of a wound to be carried out by the surgeon without resorting to an assistant for giving the surgeon disinfectant liquids, adhesive and gauze tampons in the course of the suture operation.

These and other objects which will be more apparent in the course of the description are attained, according to the invention, by a suturing gun which is characterized in that, in addition to the conventional stitch applying device, it comprises:

a control element for actuating the pliers arranged outside the gun and in a position easily accessible by the surgeon's hand;

driving means for transmitting movement of the control element to the pliers (or clamping means);

housing means for containing and retaining gauze tampons;

first dispensing means for containing and dispensing a disinfectant liquid; and second dispensing means for containing and dispensing a suture adhesive.

BRIEF DESCRIPTION OF THE DRAWINGS

FIG. 1 is a perspective view of a suturing gun, according to the present invention, in a rest position;

FIG. 2 is a view similar to FIG. 1, but with forceps shown in a closed position for bringing together the wound margins;

FIG. 3 is a view similar to FIG. 2, with the gun in an active position for delivering the suture stitches;

FIG. 4A is a side view of a driving system for actuating the forceps, with the forceps shown in an open position;

FIG. 4B is a plan view of the driving system for actuating the forceps of FIG. 4A;

FIG. 5A is a side view of the driving system for actuating the forceps, with the forceps shown in the closed position;

FIG. 5B is a plan view of the driving system for actuating the forceps of FIG. 5A; and FIG. 6 is a side elevation view of the suturing gun according to the present invention, partially sectioned to show a disinfectant container, an adhesive pump and a container for gauze tampons.

DESCRIPTION OF THE PREFERRED EMBODIMENT

Referring now to FIGS. 1 to 3, there is shown a mechanical automatic suturing gun according to the invention which comprises a grip 1, a body 2, a tip 3, and a trigger 4. Such elements are conventional elements of suturing guns.

The tip 3 includes a slit 8 (see FIG. 3) through which, upon operating the trigger 4, suture stitches S are delivered. Pliers P which are formed of a pair of toothed jaws 5, 6 are then applied to a delivered suture. The jaws 5, 6 are pivotally connected to each other and controlled, through a mechanical driving system which will be described later, by a control element 7 arranged outside the gun body 2 and above the trigger 4. The jaws 5, 6 of the pliers P are slanted with respect to the longitudinal axis of the gun.

In FIG. 1 the suturing gun is shown in a rest position in which the jaws 5, 6 of the pliers P are open and the trigger 4 and the control element 7 are in the rest position.

In FIG. 2 the suturing gun is shown in a position in which it clamps the wound margins, wherein the jaws 5, 6 of the pliers P have been closed by the control element 7 which has been moved from position A (phantom lines) to position B (solid lines), while the trigger 4 is in the rest position.

In FIG. 3 the suturing gun is shown in a suturing position with the jaws 5, 6 of the pliers P being in a closed position in which they maintain the wound margins therebetween and with the trigger 4 being moved from the position C (phantom lines) to the position D (solid lines), so that the suture stitch S is applied to the converged wound margins, thereby suturing the wound. The control element 7 extends through the body 2 of the suturing gun through a slot 9 and is provided at the outer end thereof with a lug 10 which acts as a grip element for a surgeon's finger.

In FIGS. 4A, 4B, 5A and 5B there is shown the driving system for actuating the pliers P. In FIGS. 4A and 4B the pliers are shown in an open position and in FIGS. 5A and 5B the pliers are shown in a closed position. The control element 7 is formed of a two-arm lever which is pivotally mounted on a pivot 11 and which includes an arm 12 which extends outward and is provided with a lug 10, and an arm 13 which is provided at its end with a slot 14 adapted to receive a pin 15 fastened on an arm 16 of a bell crank 17 pivotally mounted on a pivot 18. The other arm 16a of the bell crank 17 is also provided with a pin 19 to which a tie rod 20 is connected. The tie rod 20 has at its free end a plate 21 provided with a pair of transverse and aligned slots 22 and 23. Also connected to the pin 19 of the bell crank 17 is one end of a tension coil spring 24 which is fastened at its other end to the gun body 2.

The jaws 5, 6 of the pliers are pivotally connected to each other by a pivot connection 25 connecting portions 26 and 27. Each of the portions 26 and 27 are substantially disc-shaped and together form the pivot portion of the pliers. The disc 26 is provided with a downwardly extending post 28 adapted to engage in the slot 22 of the plate 21 of the tie rod 20 and the disc 27 is provided with a downwardly extending post 29 adapted to engage in the slot 23 of the plate 21 of the tie rod 20.

When the control element 7 is lowered by downward force against the lug 10, the lever arm 13 rotates in a counterclockwise direction, so that the bell crank will rotate in a clockwise direction and the tie rod 20 will be pulled rearwardly into the gun against the force of the tension spring 24. This rearward movement of the tie rod 20 causes rearward movement of the plate 21 and, in turn, causes the posts 28, 29 of the discs forming the pivot portion of the pliers P to move in the respective slots 22 and 23 from outer positions to inner positions, so that the disc 26 will rotate in a clockwise direction and the disc 27 will rotate in a counterclockwise direction (FIG. 4B). This rotary movement will cause the jaws 5, 6 of the pliers P to swing until they reach the closed position (FIG. 5B). In this position the jaws 5, 6 will maintain the wound margins clamped together.

When the control element 7 is released, the tension spring 24 will return all the components of the driving system just described to their initial positions, i.e. to the rest position of the suturing gun (see FIG. 1), in which the jaws 5, 6 of the pliers P are in the open position.

FIG. 6 illustrates the suturing gun in partial longitudinal cross section, such that the driving system for actuating the pliers is not shown therein. This Figure illustrates three additional features of the suturing gun according to the invention, as arranged in the grip 1 thereof.

More particularly, in the bottom of the grip 1, a hole 30 is provided which opens into a lower chamber 31 which has resilient tongues 32 arranged at least along opposing walls thereof. The function of this chamber 31 is to receive one or more gauze tampons, not shown, whereas the function of the resilient tongues 32 is to retain these gauze tampons in the chamber 31. The gauze tampons are inserted in the hole 30 of the chamber 31 by hand, preferably at the time that the suturing gun is to be used.

Another chamber 33 is provided in the upper portion of the gun grip 1 and is intended to receive a disinfectant liquid or the like. More particularly, the chamber 33 has an inlet hole 34 in the rear wall of the gun, which is provided with a check valve 35, and a capillary hole 36 in a wall opposite the rear wall. The function of the capillary hole 36 is to let the disinfectant liquid flow by gravity when the suturing gun is in the vertical or use position such that the disinfectant liquid passes from the capillary hole 36, through the gun body 2 and from the slit 8 from which the stitches S are dispensed, thereby disinfecting the wound margins during the suturing operation. The chamber 33 can be filled with disinfectant liquid by inserting through the inlet hole 34 the needle of a syringe, which opens the check valve 35 and then injects the disinfectant liquid into the chamber 33. Once the syringe needle has been removed from the hole 34 the check valve 35 automatically closes.

In the grip 1, between the upper chamber 33 and the lower chamber 31, a further chamber 37 is provided, in which a container 39 of suture adhesive and a small suction pump 38 are arranged. The suction pump 38 is connected to the container 39 by a flexible tube 42 which extends into the container 39. A piston 40 of the suction pump 38 abuts the rear edge of the gun trigger 4. The delivery side of the pump 38 communicates through a flexible tube 41 with a spout 43 disposed adjacent the slot 8 from which the suture stitches S are dispensed. With this arrangement, when the trigger 4 is pulled to deliver a suture S from the outlet slit 8, the suction pump 38 is simultaneously actuated, such that the suture adhesive is sucked from the container 39, through the flexible tube 42 and then delivered through the flexible tube 41 and out of the opening 43 onto the sutured wound.

By means of this suturing gun the surgeon, using only one hand, can clamp the wound margins together by pressing the control element 7 and then apply the stitches for suturing the wound margins so clamped by pulling the trigger 4. In the meantime, the wound to be sutured is subjected to the action of the disinfectant liquid or the like which flows from the capillary hole 36. Additionally, the suture adhesive is dispensed onto the wound during application of the stitch.

From the foregoing it is readily apparent that the suturing gun according to the invention offers the following advantages.

(1) The surgeon has one hand free during the suturing operation such that it is less likely that he will need an assistant as is necessary with known suturing guns;

(2) the gun is provided with pliers for clamping the wound margins, which pliers can be actuated by the surgeon with one hand, thereby facilitating the suturing operation;

(3) The gun is provided with a housing for gauze tampons such that they are readily available to the surgeon during the suturing operation and can be reached by the surgeon with his free hand;

(4) the gun is provided with a small reservoir of disinfectant liquid or the like such that it is no longer necessary to have an additional operator to supply to the surgeon or perhaps apply the disinfectant liquid onto the wound;

(5) the gun is provided with a small reservoir for the suture adhesive, which can be pumped onto the wound as the gun trigger is pulled.

While the present invention has been described in connection with a preferred embodiment thereof, it is apparent that those skilled in the art can make various modifications and changes without departing from the scope of the invention. In particular, the driving system for actuating the pliers could be made in a manner other than that illustrated and the suturing gun of the invention could alternatively include one, two or all the additional feature described above.

What is claimed is:

1. Automatic mechanical suturing gun having a gun body and in which a trigger is provided to allow a surgeon to cause delivery and application of suture stitches through an outlet of the gun body to a wound, comprising:

clamping means for clamping together the margins of the wound, said clamping means being arranged adjacent the outlet;

control means, mounted externally of the gun body in a position easily accessible to the surgeon, for actuating said clamping means;

driving means for transmitting movement of said control means to said clamping means;

housing means for containing and retaining gauze tampons;

first dispensing means for containing and dispensing a disinfectant liquid; and second dispensing means for containing and dispensing a suture adhesive.

2. A suturing gun as recited in claim 1, wherein said clamping means comprises a pair of toothed jaws and said driving means comprises a linkage mounted inside the gun body and connected to said control means.

3. A suturing gun as recited in claim 2, wherein said linkage comprises a lever having a first arm connected to said control means and a second arm, a bell crank having a first arm pivotally connected to said second arm of said lever and a second arm, and a tie rod pivotally connected at a first end to said second arm of said bell crank and connected at a second end to said clamping means for controlling said toothed jaws.

4. A suturing gun as recited in claim 3, wherein said clamping means further comprises a pivot portion which includes a first disc connected to one of said toothed jaws and a second disc connected to the other of said toothed jaws, said first and second discs being rotatably connected to one another.

5. A suturing gun as recited in claim 4, wherein said second end of said tie rod has two slots formed therein; and each of said first and second discs has a post projecting therefrom and engaged in one of said two slots in said second end of said tie rod;

such that when said tie rod is moved rearwardly by actuation of said control means, said first and second discs are caused to rotate relative to one another, thereby causing said toothed jaws to move toward a closed position.

6. A suturing gun as recited in claim 5, wherein a return spring means for returning said toothed jaws to an open position.

7. A suturing gun as recited in claim 1, wherein the gun body includes a gun grip; and said housing means for containing and retaining said gauze tampons comprises a chamber formed in said gun grip, and tongues mounted in said chamber for retaining said gauze tampons.

8. A suturing gun as recited in claim 1, wherein the gun body includes a gun grip; and said first dispensing means comprises a disinfectant reservoir formed in said gun grip and means for delivering the disinfectant liquid to the wound.

9. A suturing gun as recited in claim 8, wherein said means for delivering said disinfectant liquid is operable to cause said disinfectant liquid to flow to the wound under the force of gravity.

10. A suturing gun as recited in claim 9, wherein said disinfectant reservoir includes an inlet hole provided with a check valve, and a capillary hole communicating with the outlet of the gun body.

11. A suturing gun as recited in claim 1, wherein said second dispensing means comprises an adhesive reservoir, a pump communicating with said adhesive reservoir, and means for actuating said pump upon actuation of the gun trigger so as to dispense the adhesive to the wound when a suture stitch is applied to the wound.

12. A suturing gun as recited in claim 11, wherein said pump comprises a suction pump.

* * * * *